United States Patent
Zhu et al.

(10) Patent No.: US 10,960,122 B2
(45) Date of Patent: Mar. 30, 2021

(54) SYSTEM AND METHOD OF MONITORING AND CONTROL OF ULTRAFILTRATION VOLUME DURING PERITONEAL DIALYSIS USING SEGMENTAL BIOIMPEDANCE

(71) Applicant: Fresenius Medical Care Holdings, Inc., Waltham, MA (US)

(72) Inventors: Fansan Zhu, Flushing, NY (US); Nathan W. Levin, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 481 days.

(21) Appl. No.: 14/405,549

(22) PCT Filed: Jun. 7, 2013

(86) PCT No.: PCT/US2013/044795
§ 371 (c)(1),
(2) Date: Dec. 4, 2014

(87) PCT Pub. No.: WO2013/185080
PCT Pub. Date: Dec. 12, 2013

(65) Prior Publication Data
US 2015/0133854 A1    May 14, 2015

Related U.S. Application Data

(60) Provisional application No. 61/657,271, filed on Jun. 8, 2012.

(51) Int. Cl.
*A61M 1/28*    (2006.01)
*A61B 5/145*    (2006.01)
*A61B 5/00*    (2006.01)

(52) U.S. Cl.
CPC ............. *A61M 1/28* (2013.01); *A61B 5/1451* (2013.01); *A61B 5/4848* (2013.01); *A61M 1/281* (2014.02);
(Continued)

(58) Field of Classification Search
CPC ........ A61M 1/28; A61M 1/281; A61M 1/282; A61M 1/284; A61B 5/1451; A61B 5/4848
(Continued)

(56) References Cited

U.S. PATENT DOCUMENTS 5,902,336 A    5/1999  Mishkin
7,228,170 B2   6/2007  Zhu et al.
(Continued)

FOREIGN PATENT DOCUMENTS

CN    87212650 U    12/1988
WO    2009134878 A1    11/2009
(Continued)

OTHER PUBLICATIONS

Notification of Transmittal of the International Search Report and the Written Opinion of the International Searching Authority for PCT/US2013/44795, "System and Method of Monitoring and Control of Ultrafiltration Volume During Peritoneal Dialysis Using Segmental Bioimpedance"; dated Sep. 9, 2013.
(Continued)

*Primary Examiner* — Jenna Zhang

(57) ABSTRACT

A peritoneal dialysis (PD) system for infusing a volume of PD solution into a patient's peritoneal cavity in order to perform peritoneal dialysis on the patient includes a peritoneal cavity monitor (PCM) that measures this volume of fluid in the patient's peritoneal cavity by segmental bioimpedance spectroscopy (SBIS), to thereby determine an ultrafiltration volume of fluid in the patient's peritoneal cavity, and a switch, controlled by the PCM, for filling the patient's peritoneal cavity and draining the patient's peritoneal cavity when the ultrafiltration volume is unchanged over time, significantly decreased, or decreasing at a significant rate.

7 Claims, 7 Drawing Sheets

(52) U.S. Cl.
CPC ............ *A61M 1/282* (2014.02); *A61M 1/284* (2014.02); *A61B 5/6866* (2013.01); *A61M 2205/17* (2013.01); *A61M 2205/18* (2013.01); *A61M 2205/3317* (2013.01); *A61M 2205/3344* (2013.01); *A61M 2205/3379* (2013.01); *A61M 2205/3569* (2013.01); *A61M 2205/3592* (2013.01); *A61M 2210/1017* (2013.01); *A61M 2230/005* (2013.01)

(58) Field of Classification Search
USPC .......................................................... 604/28
See application file for complete search history.

(56) References Cited

U.S. PATENT DOCUMENTS

| | | | | |
|---|---|---|---|---|
| 7,354,417 | B1* | 4/2008 | Levin | A61B 5/107 604/29 |
| 9,078,971 | B2* | 7/2015 | Scarpaci | A61M 1/166 |
| 2003/0120170 | A1 | 6/2003 | Zhu et al. | |
| 2006/0241543 | A1* | 10/2006 | Gura | A61M 1/1601 604/5.01 |
| 2009/0008306 | A1* | 1/2009 | Cicchello | A61M 1/1682 210/85 |
| 2009/0012457 | A1* | 1/2009 | Childers | A61M 1/1605 604/29 |
| 2009/0131858 | A1 | 5/2009 | Fissell et al. | |
| 2009/0182204 | A1* | 7/2009 | Semler | G16H 40/63 600/301 |
| 2010/0191181 | A1* | 7/2010 | Childers | A61M 1/28 604/29 |
| 2011/0093294 | A1* | 4/2011 | Elahi | G16H 20/40 705/3 |
| 2015/0133854 | A1 | 5/2015 | Zhu et al. | |

FOREIGN PATENT DOCUMENTS

| | | |
|---|---|---|
| WO | WO 2011/046797 A1 | 4/2011 |
| WO | WO 2011/094113 A1 | 8/2011 |
| WO | WO 2013/185080 A1 | 12/2013 |

OTHER PUBLICATIONS

Notification Concerning Transmittal of International Preliminary Report on Patentability for PCT/US2013/44795, "System and Method of Monitoring and Control of Ultrafiltration Volume During Peritoneal Dialysis Using Segmental Bioimpedance"; dated Dec. 18, 2014.

* cited by examiner

US 10,960,122 B2

SYSTEM AND METHOD OF MONITORING AND CONTROL OF ULTRAFILTRATION VOLUME DURING PERITONEAL DIALYSIS USING SEGMENTAL BIOIMPEDANCE

RELATED APPLICATION

This application is the U.S. National Stage of International Application No. PCT/US2013/044795, filed Jun. 7, 2013, which designates the U.S., published in English, and claims the benefit of U.S. Provisional Application No. 61/657,271, filed on Jun. 8, 2012. The entire teachings of the above applications are incorporated herein by reference.

BACKGROUND OF THE INVENTION

Renal dysfunction or failure and, in particular, end-stage renal disease, causes the body to lose the ability to remove water and minerals and excrete harmful metabolites, maintain acid-base balance, and control electrolyte and mineral concentrations within physiological ranges. Toxic uremic waste metabolites including urea, creatinine, uric acid, and phosphorus accumulate in the body's tissues, which can result in a person's death if the filtration function of the kidney is not replaced.

Dialysis is commonly used to replace kidney function by removing these waste toxins and excess water. In one type of dialysis treatment, peritoneal dialysis (PD), sterile, pyrogen-free dialysis solution is infused into the patient's peritoneal cavity. The peritoneal membrane serves as a natural dialyzer and toxic uremic waste metabolites and various ions diffuse from the patient's bloodstream across the membrane into the dialysis solution due to their concentration gradients. At the same time, fluid is drawn into the peritoneal cavity by an osmotic gradient. The dialysis solution is removed, discarded and replaced with fresh dialysis solution on a semi-continuous or continuous basis.

In the routine care of patients on peritoneal dialysis, removal of fluid by ultrafiltration plays a significant role in maintenance of normal body fluid volume and blood pressure. See Arkouche W., Fouque D., Pachiaudi C., Normand S., Laville M., Delawari E., Riou J. P., Traeger J., and Laville M., Total body water and body composition in chronic peritoneal dialysis patients, J Am Soc Nephrol 8: 1906-1914, 1997; Lindholm B., Werynski A., and Bergström J., Fluid transport in peritoneal dialysis, Int J Artif Organs 13:352-358, 1990; and Korbet M. S., Evaluation of ultrafiltration failure, Advances in Renal Replacement Therapy 5(3):194-204, 1998. The ability of the peritoneal membrane to remove fluid volume is typically assessed by the standard peritoneal equilibration test (PET), which measures the dialysate to plasma (D/P) ratio of selected substance (solute) concentrations, such as creatinine. For each solute, the transport rate is categorized as low, low average, high average, and high, in increasing ranges of the D/P ratio. See Twardowski Z. J., Nolph K. O., Khanna R., Prowant B. F., Ryan L. P., Moore H. L., and Nielsen M. P., Peritoneal Equilibration Test, Perit Dial Bull 7: 138-147, 1987; and Smit W., Estimates of peritoneal membrane function-new insights, Nephrol Dial Transplant 21: ii16-ii19, 2006 (hereinafter "Smit"). A high D/P ratio of creatinine is a reflection of ultrafiltration failure, as it is related to high absorption rates of low molecular weight osmotic agents, such as glucose, from the dialysate into the patient's blood, and therefore to a rapid disappearance of the osmotic gradient that enables removal of fluid from the patient into the dialysate. See Smit. After the disappearance of the osmotic gradient, fluid from the dialysate can be reabsorbed across the peritoneal membrane back into the patient. In such hyper-absorbing patients, the drain volume can be less than the initial filling volume, and is certainly less than the maximal desirable ultrafiltration volume. However, PET cannot be used to monitor the ability of the peritoneal membrane to remove fluid volume while a PD treatment is being administered. Traditionally, the total ultrafiltration volume (UFVM) is determined from the difference in weight between total filling and draining volumes at the end of a PD treatment, and therefore hyper-absorbing patients cannot be identified earlier in the treatment cycle.

Therefore, there is a need for improved monitoring of fluid removal by ultrafiltration for patients on peritoneal dialysis.

SUMMARY OF THE INVENTION

The present invention generally relates to peritoneal dialysis of a patient.

In one embodiment, a peritoneal dialysis (PD) system for infusing a volume of PD solution into a patient's peritoneal cavity in order to perform peritoneal dialysis on the patient includes a peritoneal cavity monitor (PCM) that measures the volume of fluid in the patient's peritoneal cavity by segmental bioimpedance spectroscopy (SBIS), to thereby determine an ultrafiltration volume of fluid in the patient's peritoneal cavity, and a switch, controlled by the PCM, for filling the patient's peritoneal cavity and draining the patient's peritoneal cavity when the ultrafiltration volume is unchanged over time, significantly decreased, or decreasing at a significant rate. Alternatively, instead of the switch, the peritoneal dialysis (PD) system can include an alarm, controlled by the PCM, for indicating when the patient's peritoneal cavity is to be drained when the ultrafiltration volume is unchanged over time, significantly decreased, or decreasing at a significant rate.

In another embodiment, a method of peritoneal dialysis of a patient includes introducing a volume of peritoneal dialysis solution into the peritoneal cavity of the patient, and measuring periodically the volume of fluid in the patient's peritoneal cavity by segmental bioimpedance spectroscopy (SBIS), to thereby determine an ultrafiltration volume of fluid in the patient's peritoneal cavity. The method then includes draining the patient's peritoneal cavity when the ultrafiltration volume is unchanged over time, significantly decreased, or decreasing at a significant rate. The method can include refilling the peritoneal cavity of the patient with another volume of peritoneal dialysis solution.

The invention has many advantages, including the ability to drain the peritoneal cavity of a patient after a measured volume of fluid has accumulated therein, to minimize fluid reabsorption back into the patient, which is undesirable, thereby enabling interrupting the dialysis treatment cycle after a desired volume of fluid has been removed from the patient, or recognizing a significant reduction in ultrafiltration volume before this volume is further reduced by reabsorption back into the patient, and draining the peritoneal cavity and refilling it with another volume of dialysis fluid and continuing the dialysis treatment.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
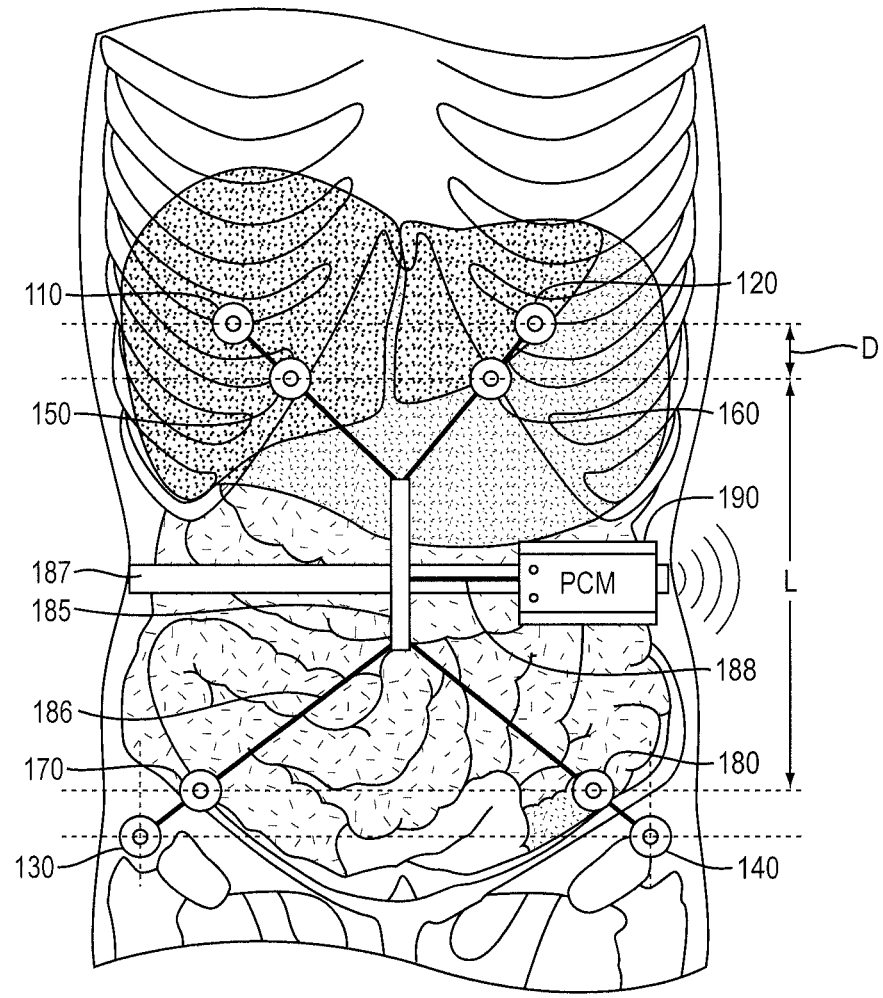
FIG. 1 is a schematic illustration of an exemplary placement of electrodes for measurement of fluid volume in the peritoneal cavity.

The present invention generally relates to peritoneal dialysis of a patient. A method of peritoneal dialysis of a patient includes introducing a volume of peritoneal dialysis fluid into the peritoneal cavity of the patient. Any suitable peritoneal dialysis solution (i.e., peritoneal dialysis fluid) known in the art (e.g., Delflex®, Fresenius Medical Care North America, Waltham Mass.) can be used. The volume of PD fluid can be in a range of between about 1.5 L and about 2.5 L, preferably about 2 L. This known volume is used to calibrate the bioimpedance measurement of volume. The method includes measuring periodically the volume of fluid in the patient's peritoneal cavity during the PD treatment time, for example at time intervals of about 1 minute, about 5 minutes, about 30 minutes, etc. More frequent measurements provide a higher temporal resolution, enabling the detection of rapid changes in ultrafiltration volume. The fluid volume measurements are made by segmental bioimpedance spectroscopy (SBIS). See Zhu F., Hoenich N. A., Kaysen G., Ronco C., Schneditz D., Murphy L., Santacroce S., Pangilinan A., Gotch F., and Levin N. W., Measurement of Intraperitoneal Volume by Segmental Bioimpedance Analysis During Peritoneal Dialysis, American Journal of Kidney Diseases, 42: 167-172, 2003 (hereinafter "Zhu et al."); and U.S. Pat. No. 7,354,417 to Levin et al. 2008. In this SBIS method, eight electrodes 110, 120, 130, 140, 150, 160, 170, and 180 (e.g., standard ECG electrodes) are placed on the body, as shown in FIG. 1. Four electrodes 110, 120, 130, and 140 are electrodes for injecting current. Electrodes 150 and 170, and 160 and 180 are two pairs of electrodes for measurement of the voltage between distance L. The distance between injecting and measurement electrodes is D. A cable holder 185 can be used to fix the electrodes cable 186 with a band 187. The volume V of fluid in the peritoneal cavity is determined based on the relationship $$V = \frac{K_p}{\sigma}\left(\frac{L^2}{R}\right) \quad (1)$$

where $K_p$ is a subject-specific calibration constant, $\sigma$ is the conductivity of the fluid in the peritoneal cavity, and R is the average of $R_L$ and $R_R$, where $R_L = \Phi_L/I$ and $R_R = \Phi_R/I$, where $\Phi_L$ is the voltage measured between electrodes 160 and 180, and $\Phi_R$ is the voltage measured between electrodes 150 and 170 upon injection of current I between electrodes 120 and 140 (left), and electrodes 110 and 130 (right), respectively. $K_p$ can be determined by obtaining $R_{LB}$ and $R_{RB}$ before any fluid is introduced into the peritoneal cavity, and then obtaining $R_{LA}$ and $R_{RA}$ after a predetermined volume $V_C$ of fluid (e.g., 2 L) is introduced into the peritoneal cavity of the patient, wherein $V_C$ is the change in fluid volume ($\Delta V$) between time A and time B, and then determining $K_p$ from the equation $$K_p = \sigma \frac{V_C}{L^2}\left(\frac{R_B R_A}{R_B - R_A}\right) \quad (2)$$

where $R_B = (\Phi_{LB} + \Phi_{RB})/(2I)$ and $R_A = (\Phi_{LA} + \Phi_{RA})/(2I)$.

Figure 2:
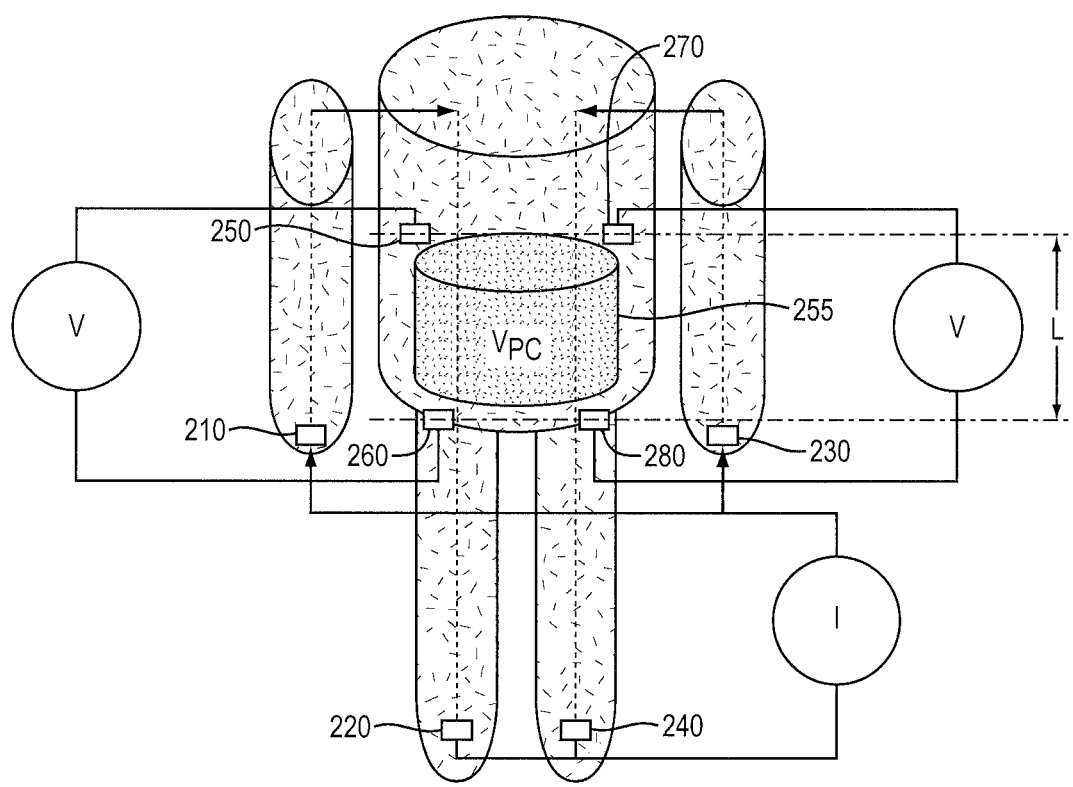
FIG. 2 is a schematic illustration of another exemplary placement of electrodes and measurement of fluid volume in the peritoneal cavity.

Alternatively, SBIS can be performed using a Hydra bioimpedance device, modified as described below, with the patient in a supine body position, for example during a standard PET. See Zhu et al.; Hydra 4200 Analyzer, Xitron Technologgies Inc., San Diego, Calif. As shown in FIG. 2, the method includes four electrodes 210, 220, 230, and 240 for injecting current placed on each hand (210, and 230) and foot (220 and 240), respectively, and four measuring electrodes 250, 260, 270, and 280 placed on the lower ribs (250 and 270) and the buttocks (260 and 280) on both sides of the body. An alternating current (e.g., 5 kHz, in a range of between about 0.05 mA and about 0.7 mA) is injected continuously during measurement. With this arrangement of the sensors, the injected current penetrates the peritoneal cavity on both sides of the body. The Hydra 4200 Analyzer can be used for measuring only one segment, and therefore the analyzer was modified by the addition of a switch (not shown) between segments on either side of the body. The length of the segment L between electrodes 250 and 260 on one side and electrodes 270 and 280 on the other side can be measured, for example with a flexible tape. The segmental extracellular volume V contained within the region of interest 255 is calculated from $$V = \frac{K_s}{\sigma}\left(\frac{L^2}{R}\right) \quad (3)$$

where R is the average segmental resistance measured between the two sides of the body across the length L, and $\sigma$ is the conductivity of the extracellular volume (21.28 mS/cm), and $K_s$ is a calibration factor determined from the first filling volume ($V_1$) and the resistance of the empty ($R_E$) and the filled peritoneal cavity ($R_F$) using the equation $$K_s = \frac{\sigma V_1}{L^2\left(\frac{1}{R_F} - \frac{1}{R_E}\right)} \quad (4)$$

Figure 3:
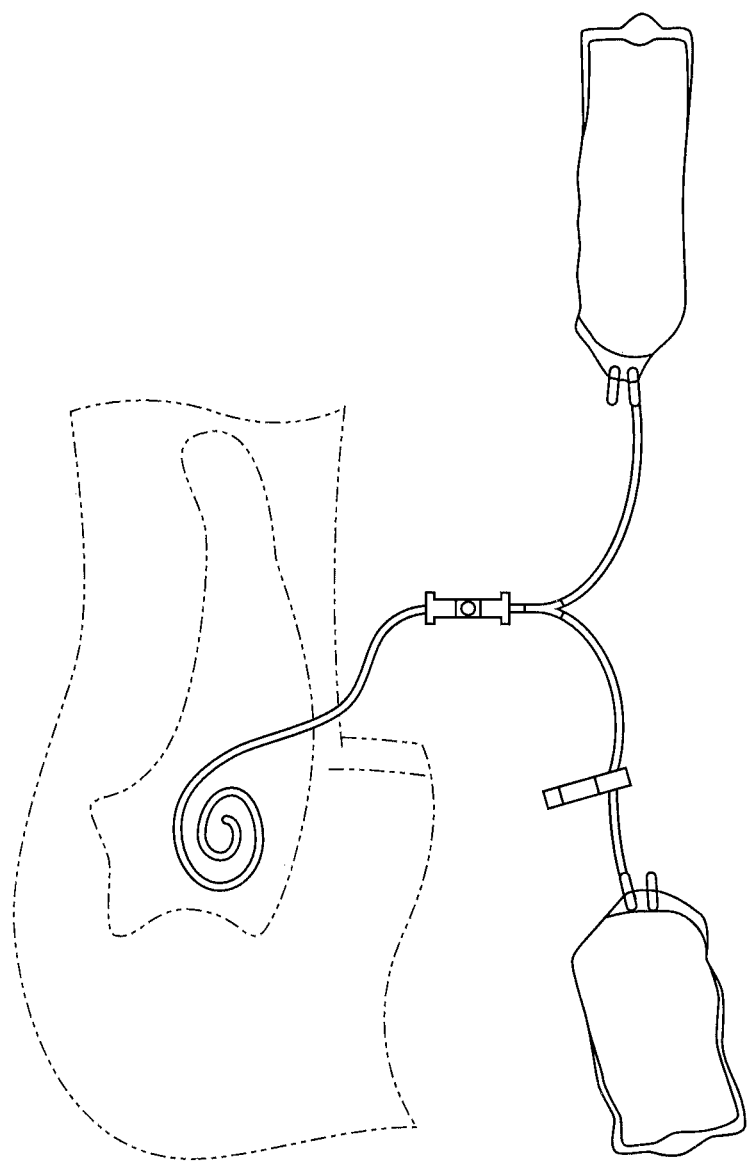
FIG. 3 is a side view of the electrodes shown in FIG. 2 and the peritoneal cavity of a patient in a sitting position.

Calibration of the SBIS method to establish the relationship between change in resistance and fluid volume in the peritoneal cavity 255 is performed by introducing, as shown in FIG. 3, a known volume of dialysate at the beginning of treatment. The calibration factor $K_s$ for this method can be different from the calibration factor $K_p$ for the eight electrode method described above. The increase of fluid volume in the peritoneal cavity during dwell time is considered to be equal to the net ultrafiltration volume (UFVSBIS) occurring during this period. Drain volume (DVM) is measured by weighing the last drain volume.

Figure 4:
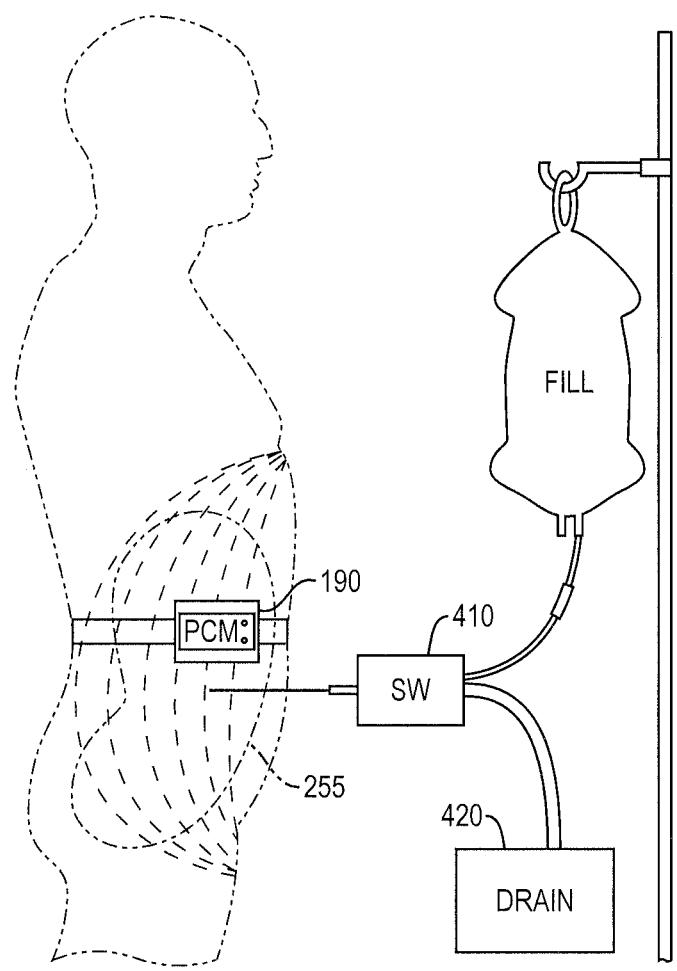
FIG. 4 is a schematic illustration of PD treatment and dialysate control. A switch (SW) is used to control drain or fill of fluid from or into the peritoneal cavity according to a signal from the peritoneal cavity monitor (PCM).

Turning back to FIG. 1, a connecting cable 188 is used to transfer signals from the electrodes to the peritoneal cavity monitor (PCM) 190. The PCM is used to measure the impedance and transfer a wireless signal, described further below, to control the switch (SW) 410 shown in FIG. 4 to fill or drain the peritoneal cavity 255 into drain 420. Alternatively, for use in nonautomated PD (e.g., continuous ambulatory peritoneal dialysis (CAPD)), an audible or vibrating alarm can alert the patient or attendant to drain immediately. After the first drain of fluid out of the peritoneal cavity 255, and the infusion of 2 liters of fluid into the peritoneal cavity 255 for the typical four hours of dwell time, the volume of fluid in the peritoneal cavity 255 is periodically monitored by SBIS, to monitor the fluid volume in the peritoneal cavity ($V_{PC}$). The peritoneal cavity 255 can be drained when the volume in the peritoneal cavity 255 has reached a maximal volume, or when the volume in the peritoneal cavity 255 significantly decreases, such as a relative volume decrease equal to or greater than about 0.3 L, or when the volume in the peritoneal cavity 255 significantly decreases over a time interval, such as more than 10 minutes, or remains stable (i.e., unchanged) for a period of time, in a range of between about 10 minutes and about 30 minutes, preferably about 10 minutes, after which time a new PD dialysate volume (e.g., 2 L) can be infused, until the end of the treatment (typically four hours). A significant rate of decrease in the volume of fluid in the peritoneal cavity 255 can be a rate of volume decrease equal to or greater than about 0.03 L/min. Alternatively, a significant decrease in the volume of fluid in the peritoneal cavity 255 can be a relative volume decrease equal to or greater than about 0.3 L.

Figure 5:
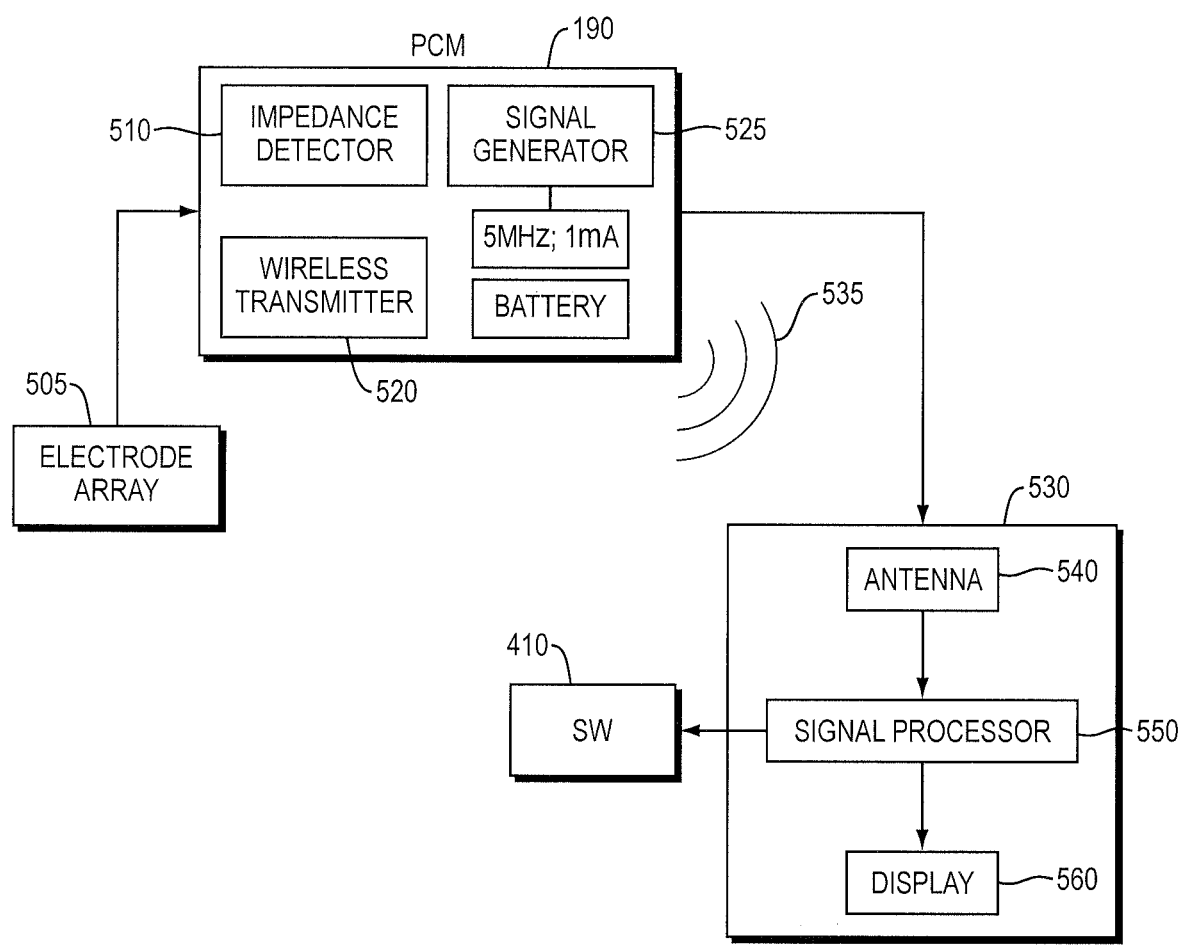
FIG. 5 is a block diagram of an example of a device for measurement and control of the peritoneal dialysis treatment.
Figure 6:
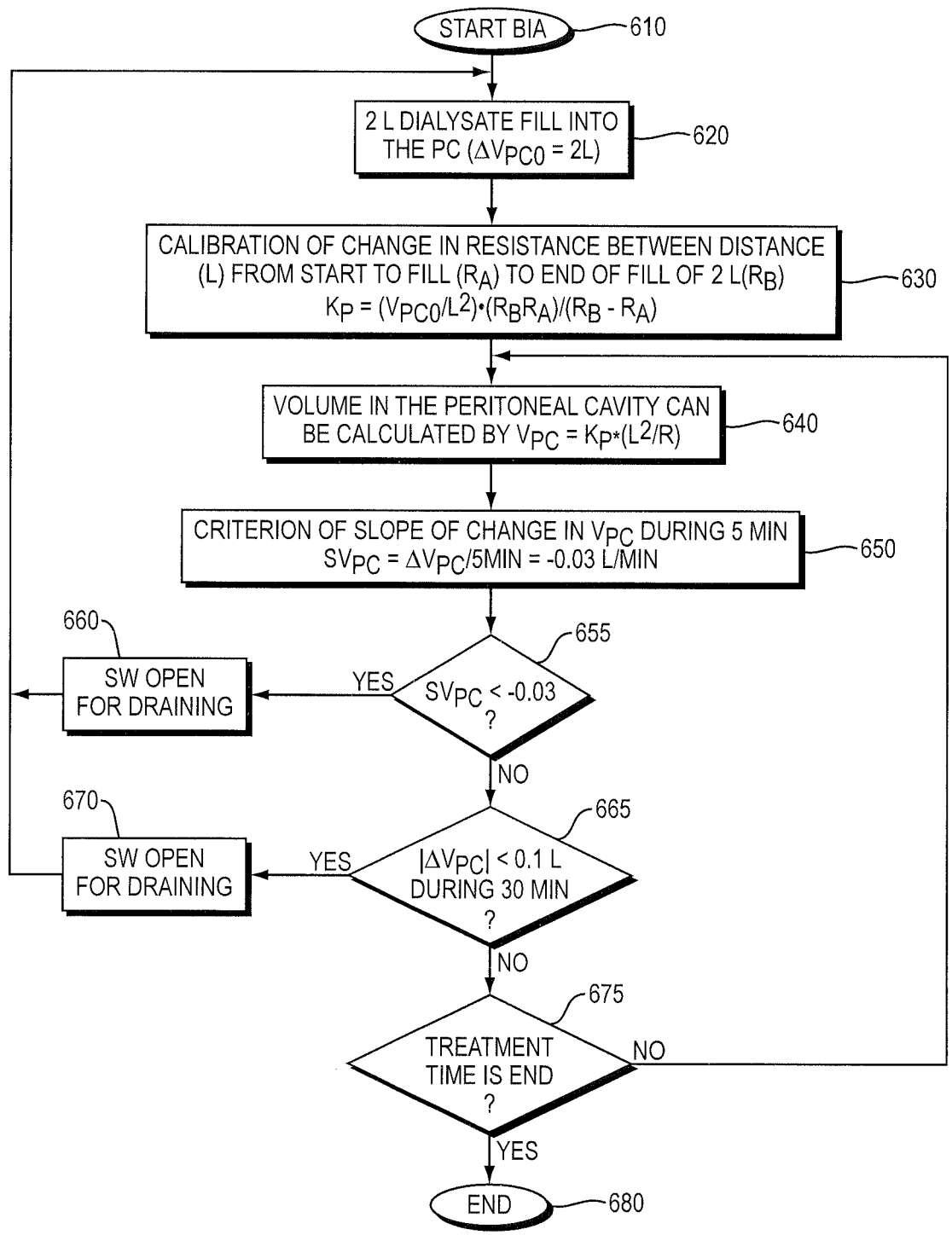
FIG. 6 is a flowchart for determining fluid exchange during PD treatment using SBIS.

As illustrated in FIG. 5, the PCM 190 continuously collects impedance data from electrode array 505 within a low frequency range (e.g., between about 1 kHz and about 300 kHz) (impedance detector 510). A wireless transmitter 520 can be used, using a high frequency signal produced by signal generator 525 (e.g., 5 MHz), to send the impedance signal 535 to the receiver 530. The receiver 530 obtains the impedance signal 535 from an antenna 540 and employs a signal processor 550 to determine whether the switch (SW) 410 should be open or closed for filling or draining according to the flow chart shown in FIG. 6, displaying the result on display 560. As shown in FIG. 6, the method starts with bio-impedance analysis (BIA) of the patient at step 610, followed by a dialysate fill, at step 620, into the peritoneal cavity of the patient of a predetermined volume (e.g., 2 L). Then, step 630 is a calibration of the change in resistance across the distance L from the start of fill to the end of fill, to determine $K_p$. The volume of dialysate in the peritoneal cavity is subsequently calculated at step 640, and the criterion of slope of change in $V_{PC}$ during 5 minutes, $SV_{PC}$, is established at step 650. If $SV_{PC}$ is less than a threshold level (e.g., 0.03 L/min) at step 655, then the switch 410 (SW) is opened for draining at step 660. If the absolute value of the change in $V_{PC}$ ($\Delta V_{PC}$) is less than a predetermined amount (e.g., 0.1 L) during a 30 min period at step 665, then the switch 410 (SW) is opened for draining at step 670. If neither of the conditions 655 and 665 are met, then the treatment continues until, at step 675, the treatment time is finished, and the treatment ends at step 680. A person of skill in the art, such as a physician or a nurse, can adjust or devise different conditions for draining as appropriate for a particular patient based on the description provided herein.

The PCM can be integrated into a peritoneal dialysis (PD) system, such as the Liberty® Cycler, that can include a volume of PD solution to be infused into a patient's peritoneal cavity in order to perform peritoneal dialysis on the patient, the peritoneal cavity monitor (PCM) to measure the volume of fluid in the patient's peritoneal cavity by segmental bioimpedance spectroscopy (SBIS), to thereby determine an ultrafiltration volume of fluid accumulated in the patient's peritoneal cavity, and the switch, controlled by the PCM, for filling the patient's peritoneal cavity and draining the patient's peritoneal cavity when the ultrafiltration volume is unchanged, significantly decreased, or decreasing at a significant rate. Liberty® Cycler, Fresenius Medical Care North America, Waltham, Mass.; see U.S. Pat. No. 7,935,074 and U.S. application Ser. No. 12/709,039 published as US 2010/0222735 A1.

In one embodiment, the determination to drain the patient's peritoneal cavity and, optionally, exchange the dialysate (i.e., refill the patient's peritoneal cavity) during PD treatment, as shown in FIG. 6, is based on two criteria: 1) the slope of volume change in the peritoneal cavity ($SV_{PC}$) is less than about −0.03 L/min, in other words the $V_{PC}$ decreases by more than about 0.3 L during 10 minutes, or 2) $V_{PC}$ does not change during 30 minutes. During the entire treatment time, if the condition 1) or 2) is met, the switch (SW) opens automatically for draining, and, after the peritoneal cavity is drained, a new 2 L volume of dialysate will be infused into peritoneal cavity until the treatment is completed. Alternatively, an alarm (e.g., an audible or vibrating alarm) can alert the patient or attendant to trigger draining.

EXEMPLIFICATION

Segmental bioimpedance spectroscopy (SBIS) using a Hydra 4200 Analyzer modified as described above was performed with the patients in supine body position during standard PET. See Zhu et al. Four electrodes for injecting current were placed on each hand and foot. Four measuring electrodes were placed on the lower ribs and the buttocks on both sides of the body. Calibration of the SBIS method to establish the relationship between change in resistance and fluid volume in the peritoneal cavity was performed by introducing a known volume of dialysate in the beginning of treatment. The increase of fluid volume in the peritoneal cavity during dwell time was considered to be equal to the net ultrafiltration volume (UFVSBIS) occurring during this period. Drain volume (DVM) was measured by weighing the last drain volume. Dialysate creatinine concentration (DCre) was determined at time points 0, 2 hrs, and at the end. Plasma creatinine concentration (PCre) was measured at the beginning of PET. D/P was calculated by DCre/PCre.

As shown in Table 1, $UFV_{Diff}$ represents the change in net UFVSBIS between the beginning and the subsequent measurement time. UFVM (0.64, 0.63 and 0.26 L) and UFVSBIS (0.42, 0.54 and 0.05 L) were observed for each Patient 1, 2, and 3, respectively. Mean UFVM did not differ from the net UFVSBIS (0.51±0.22 vs 0.34±0.26 L) and mean DVM (2.62, 2.5 and 2.25 L for each patient) was approximately equal to the DVSBIS (2.0, 2.2 and 2.21 L for each) estimated by SBIS (2.46±0.19 vs 2.13±0.13 L).

The results shown in Table 1 provide information on the relationship between the change in UFV and transport of creatinine during PET. The availability of dynamic information on the ultrafiltration volume helps to understand the characteristics of the peritoneal membrane. The information might be useful for clinical practice, to adjust the PD procedure according to individual characteristics of the peritoneal membrane.

Additionally, the periodic measurement of the ultrafiltration volume enables draining the patient's peritoneal cavity at or near a maximum $UFV_{Diff}$, which, as shown in Table 1, occurred for Patient 1 at about 2 hours of dwell time and for Patient 2 at about 3 hours of dwell time, and also enables identifying a patient whose peritoneal membrane is absorbing fluid from the dialysate from the beginning of the treatment and therefore showing a negative $UFV_{Diff}$, such as Patient 3.

TABLE 1

Ultrafiltration volume results for 3 patients during PD treatment

| Dwell time [Hours] | $UFV_{Diff}$ [L] Patient1 | $UFV_{Diff}$ [L] Patient2 | $UFV_{Diff}$ [L] Patient3 | D/P Patient1 | D/P Patient2 | D/P Patient3 |
|---|---|---|---|---|---|---|
| 0 | 0 | 0 | 0 | 0.02 | 0.27 | 0.02 |
| 1 | 0.53 | 0.23 | −0.25 | | | |
| 2 | 1 | 1.113 | −0.5 | 0.35 | 0.71 | 0.55 |
| 3 | 0.53 | 1.98 | −0.73 | | | |
| 4 | 0.42 | 0.54 | 0.05 | 0.52 | 0.78 | 0.70 |

Optimal Dwell Time Example

Two pairs of electrodes were placed on both lateral aspects of the abdomen. Segmental spectroscopy (sBIS) was used to continuously monitor fluid changes during the dwell. UFV was calculated from the change in intraperitoneal fluid volume after 2 L PD fluid instillation. Optimal dwell time (ODT) is the time between start of PD and the point when fluid reabsorption is detected. Patients were studied twice in supine position using manual PD: 1) study1, regular procedure with 4 hours dwell time (DT), with sBIS monitored throughout the exchange; 2) study2 ODT procedure, dialysate was drained when the rate of change in fluid volume became negative (fluid being absorbed) or was flat (i.e., unchanged) for more than 10 minutes. Actual UFV (aUFV) was defined as the weight difference between drain and fill volumes.

Figure 7:
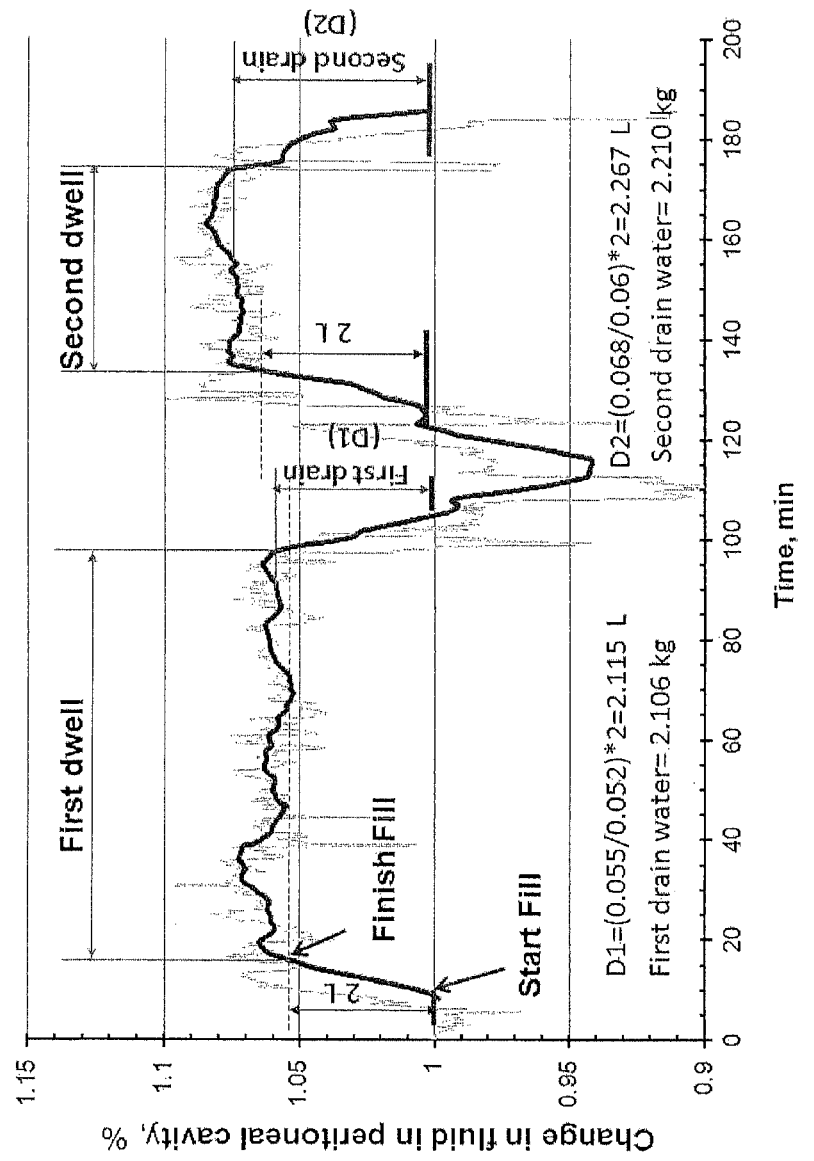
FIG. 7 is a graph of the change in fluid volume (%) in the peritoneal cavity of patient #5 as a function of time (min).

Preliminary results in the three patients (Table 2) show that aUFV was identical to UFV estimated by sBIS. In the second study, the optimal time to drain was within the first two hours of dwell. FIG. 7 shows the changes in peritoneal fluid volume during PD in patient #5.

TABLE 2

| Patient | DT, min | Study1 aUFV, L | UFV, L | ODT, min | Study2 aUFV, L | UFVMax, L |
|---|---|---|---|---|---|---|
| #4 | 240 | 0.406 | 0.4 | 120 | 0.266 | 0.226 |
| #5 | 245 | 0.04 | −0.007 | 100 | 0.106 | 0.115 |
| #6 | 212 | 0.396 | 0.327 | 87 | 0.368 | 0.312 |

By continuously monitoring changes in intraperitoneal fluid volume, sBIS allows maximization of UFV by optimizing DT. Any plateau or decrease in UFV should prompt dialysate drainage. An ODT could be provided for every exchange, which is particularly advantageous with automated PD. Although additional exchanges may be required to reach a Kt/V target, an important advantage of the technique is its ability to maximize ultrafiltration volume.

The relevant teachings of all patents, published applications and references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A continuous ambulatory peritoneal dialysis (PD) (CAPD) system for infusing a volume of PD solution into a patient's peritoneal cavity in order to perform peritoneal dialysis on the patient, the system comprising:
   a peritoneal cavity monitor (PCM) comprising an impedance detector configured to collect impedance data from an electrode array coupled to the PCM, the PCM configured to measure a volume of fluid in the patient's peritoneal cavity by segmental bioimpedance spectroscopy (SBIS) based on the collected impedance data to thereby determine an ultrafiltration volume of fluid in the patient's peritoneal cavity, the PCM configured to be worn on the patient; and
   an alarm activated by the PCM based on the collected impedance data, the alarm to alert a user to drain the patient's peritoneal cavity, the PCM to activate the alarm responsive to a determination that the patient is absorbing PD solution based on a rate of change of the ultrafiltration volume of fluid in the patient's peritoneal cavity during a peritoneal dialysis treatment,
   wherein the rate of change of the ultrafiltration volume of fluid in the patient's peritoneal cavity is less than about −0.03 L/min.

2. A method of performing continuous ambulatory peritoneal dialysis (PD) (CAPD) for a patient, the method comprising:
   introducing a volume of peritoneal dialysis solution into the peritoneal cavity of the patient; and
   via the CAPD system of claim 1:
      measuring periodically the volume of fluid in the patient's peritoneal cavity by segmental bioimpedance spectroscopy (SBIS), to thereby determine an ultrafiltration volume of fluid in the patient's peritoneal cavity; and
      alerting a user to drain the patient's peritoneal cavity using the alarm of the CAPD system responsive to a determination that the patient is absorbing PD solution based on a rate of change of the ultrafiltration volume of fluid in the patient's peritoneal cavity during the continuous ambulatory peritoneal dialysis,
   wherein the rate of change of the ultrafiltration volume of fluid in the patient's peritoneal cavity is less than about −0.03 L/min.

3. The CAPD system of claim 1, wherein the alarm is one of an audible alarm or a vibrating alarm.

4. The CAPD system of claim 1, further comprising a wireless transmitter to perform wireless communication to transmit the impedance data to a receiver.

5. The CAPD system of claim 4, the alarm activated based on the collected impedance data transmitted via the wireless communication of the PCM.

6. The CAPD system of claim 1, further comprising a band configured to be worn on the patient, the PCM arranged on the band.

7. The CAPD system of claim 6, further comprising a cable holder configured to fix a cable of each electrode of the electrode array with the band; and a connecting cable arranged on the band to transfer signals from each electrode of the electrode array to the PCM.

* * * * *